US008846365B2

(12) United States Patent
Frommer et al.

(10) Patent No.: US 8,846,365 B2
(45) Date of Patent: Sep. 30, 2014

(54) NUCLEIC ACIDS ENCODING PHOSPHATE FLUORESCENT INDICATORS AND METHODS OF USING THE SAME

(75) Inventors: Wolf B. Frommer, Stanford, CA (US); Hong Gu, Zhejiang (CN); Sylvie Lalonde, Stanford, CA (US); Arthur Grossman, Stanford, CA (US)

(73) Assignee: Carnegie Institution of Washington, Washington, DC (US)

( * ) Notice: Subject to any disclaimer, the term of this patent is extended or adjusted under 35 U.S.C. 154(b) by 1018 days.

(21) Appl. No.: 12/083,267

(22) PCT Filed: Oct. 14, 2005

(86) PCT No.: PCT/US2005/036955
§ 371 (c)(1),
(2), (4) Date: Jan. 15, 2009

(87) PCT Pub. No.: WO2007/044014
PCT Pub. Date: Apr. 19, 2007

(65) Prior Publication Data
US 2009/0311674 A1 Dec. 17, 2009

(51) Int. Cl.
*C12N 9/30* (2006.01)
*C07K 14/195* (2006.01)

(52) U.S. Cl.
CPC .................................. *C07K 14/195* (2013.01)
USPC ........................................ 435/203; 530/350

(58) Field of Classification Search
CPC ....................................................... C12N 9/2417
USPC ........................................ 435/203; 530/350
See application file for complete search history.

(56) References Cited

U.S. PATENT DOCUMENTS

| | | |
|---|---|---|
| 5,795,729 A | 8/1998 | Lee |
| 5,981,200 A | 11/1999 | Tsien |
| 5,998,204 A | 12/1999 | Tsien |
| 6,197,534 B1 | 3/2001 | Lakowicz |
| 6,277,627 B1 | 8/2001 | Hellinga |
| 6,376,257 B1 | 4/2002 | Persechini |
| 6,465,199 B1 | 10/2002 | Craig |
| 6,469,154 B1 | 10/2002 | Tsien |
| 2002/0058273 A1 | 5/2002 | Shipwash |
| 2003/0134346 A1 | 7/2003 | Amiss |
| 2004/0029129 A1 | 2/2004 | Wang |
| 2004/0118681 A1 | 6/2004 | Hellinga |
| 2005/0112685 A1 | 5/2005 | Amiss |
| 2005/0196768 A1 | 9/2005 | Campbell |

FOREIGN PATENT DOCUMENTS

| | | |
|---|---|---|
| WO | WO 00/49183 | 8/2000 |
| WO | WO 01/18237 | 3/2001 |
| WO | WO 03/025220 | 3/2003 |

OTHER PUBLICATIONS

Benson et al. "Design of bioelectronic interfaces by exploiting hinge-bending motions in proteins." Science 293: 1641-1644, 2001.
Blicharska et al. "Fluorescence quenching of Trp Repressor-Operator interaction." Journal of Protein Chemistry 18: 823-830, 1999.
Chen et al. "Protein localization in living cells and tissues using FRET and FILM." Differentiation 71: 528-541, 2003.
D' Auria et al. "Enzyme fluorescence as a sensing tool: new perspectives in biotechnology." Curr. Opin. in Biotechnol. 12: 99-104, 2001.
De et al. "Novel biosensors for the detection of estrogen receptor ligands." Journal of Steroid Biochemistry and Molecular Biology 96: 235-244, 2005.
De Lorimier et al. "Construction of a fluorescent biosensor family." Protein Science 11: 2655-2575, 2002.
Deuschle et al. "Construction and optimization of a family of genetically encoded metabolite sensors by semirational protein engineering." Protein Science 14: 2304-2314, 2005.
Dwyer et al. "Periplamsic binding proteins: a versatile superfamily for protein engineering." Current Opinion in Structural Biology 14: 495-504, 2004.
Fehr et al. "Visualization of maltose uptake in living yeast cells by fluorescent nanosensors." PNAS 99: 9846-9851, 2002.
Gaits et al. "Shedding light on cell signaling: Interpretation of FRET biosensors." Science's STKE: signal transduction knowledge environment: 165 (PE3): 1-5, 2003.
Gu et al. "A novel analytical method for in vivo phosphate tracking." FEBS Lett. 580: 5885-5893, 2006.
Gunsalus et al. "Nucleotide sequence and expression of *Escherichia coli* trpR, the structural gene for the *trp* aporepressor." PNAS 77: 7117-7121, 1980.
Jenne et al. "Real-time characterization of ribozymes by fluorescence resonance energy transfer (FRET)." Angewandte Chemie 38: 1300-1303, 1999.
Mitra et al. "Fluorescence resonance energy transfer between blue-emitting and red-shifted excitation derivatives of the green fluorescent protein." Gene 173: 13-17, 1996.
Miyawaki et al. "Fluorescent indicators for Ca2+ based on green fluorescent proteins and clamodulin." Nature 388: 882-887, 1997.
Muyan et al. "Fusion estrogen receptor proteins: toward the development of receptor-based agonists and antagonists." Molecular and Cellular Endocrinology 182: 249-263.
Nagai et al. "A variant of yellow fluorescent protein with fast and efficient maturation for cell-biological application." Nature Biotechnology 20: 87-90, 2002.
Okumoto et al. "Detection of glutamate release from neurons by genetically encoded surface-displayed FRET nanosensors." PNAS 102: 8740-8745, 2005.
Okumoto et al. "Genetically encoded sensors for ions and metabolites." Soil Sci. Plant Nutr. 50: 947-953, 2004.
Salins et al. "Phosphate binding protein as the biorecognition element in a biosensor for phosphate." Sensors and Actuators B 97: 81-89, 2004.

(Continued)

*Primary Examiner* — Tekchand Saidha
(74) *Attorney, Agent, or Firm* — Morgan Lewis & Bockius LLP

(57) ABSTRACT

Phosphate biosensors are disclosed, which comprise a phosphate binding domain conjugated to donor and fluorescent moieties that permit detection and measurement of Fluorescence Resonance Energy Transfer upon phosphate binding. Such biosensors are useful for real time monitoring of phosphate metabolism in living cells.

33 Claims, 8 Drawing Sheets

(56) References Cited

OTHER PUBLICATIONS

Schafer et al. "X-ray structures of the maltose-maltodextrin-binding protein of the thermophilic bacterium *Alicyclobacillus acidocaldarius* provide insight into acid stability of proteins." J. Mol. Biol. 335: 261-274, 2004.

Sigmund "Viewpoint: are studies in genetically altered mice out of control?" Arterioscler. Thromb. Vasc. Biol. 20: 1425-1429, 2000.

Tolosa et al. "Glucose sensor for low-cost lifetime-based sensing using a genetically engineered protein." Analytical Biochemistry. 267: 114-120, 1999.

Tsien "Building and breeding molecules to spy on cells and tumors." FEBS Lett. 579: 927-932, 2005.

Widersten et al. "Optimized heterologous expression of the polymorphic human glutathione transferase M1-1 based on silent mutations in the corresponding cDNA." Protein Expression and Purification 7: 367-371, 1996.

Wood et al. PRI-80 Database, Accession No. AI2966, Jul. 9, 2004, The Genome of the Natural Genetic Engineer *Agrobacterium tumefaciens* C58, Yoo et al. Science 294: 2317-2323, 2001.

Xu et al. "Kinetic and thermodynamic studies of purine repressor binding to corepressor and operator DNA." Journal of Biological Chemistry 273: 8058-8064, 1998.

Zhang et al. "Genetically encoded reporters of protein kinase A activity reveal impact of substrate tethering." PNAS 98: 14997-15002, 2001.

Terminal construct original version shortened version

SEQUENCE LISTING

```
<160> NUMBER OF SEQ ID NOS: 6

<210> SEQ ID NO 1
<211> LENGTH: 27
<212> TYPE: DNA
<213> ORGANISM: Synechococcus sp.

<400> SEQUENCE: 1
attggtaccg taggatttct aacagcg                                              27

<210> SEQ ID NO 2
<211> LENGTH: 27
<212> TYPE: DNA
<213> ORGANISM: Synechococcus sp.

<400> SEQUENCE: 2
ataggtaccg ttaacggtga tggaatc                                              27

<210> SEQ ID NO 3
<211> LENGTH: 1062
<212> TYPE: DNA
<213> ORGANISM: Synechococcus sp.

<400> SEQUENCE: 3
atgcgaaccc tgctttctgc tttctccctc accgctctaa cagtaggatt tctaacagcg          60
acctcggctc aagcccaaac cgtgcaaatc tccggggcgg gcgcgacctt tgcggctcct         120
ttgctgcaac gttggtttga cgcctacaac cgcaccgtag accccactgt gcaagtcagc         180
tatcagtctg tcggtagtgg tgctggccta gagcaggtga tcaatggcac tgtggacttc         240
ggcgcttccg aggcgccttt ctccggtgct cgcctggaaa gcttccgagc taaatacggc         300
tatgatcccc tacagttgcc tctggcggga ggggccatcg agtttgccta taacctgccc         360
ggcattgaag acggagagct catcctgaag cggaaaacct actgcggcat cgtgaccggc         420
gagatcactc gctgggacga cattcgcatc aaggccgaga acccaggtat agcaaacaag         480
ctgccacccc tggacatcac ctgggtacac cgctctgatg gttctgggac taccttttgtg        540 ttcaccaacc acatcagaac tgtctgccct aattggacag ccggtgctgg tacttctgtc         600
gagtggcctg ttggtattgg agcccaaggg aatgagggcg tagccgccac catcaagcag         660
gagccagggg cgattggcta cgtgaaccag tcctatgcca agctggaaaa gatggccact         720
gctcgcttgg aaaacaaagc gggcaacatt gttgagttct cgactgaggc agctacctcg         780
gcgctggatg ctcccattcc tgatgacttt gcgctgttgg tgcccgaccc tgaagggcca         840
aatgactacc caatcgtggg cttgttctgg gtgatgctgt accgcgagta tcccgatcag         900
cagaagctga ccaagctggt ggaggctctg aagtggaccc aggggccaga gggtcaagcc         960
atcaccaagg agctggacta catccctatg cctgaggcgg ttatccagcg gatctttgca        1020
gagctggatt ccatcaccgt taaccccaat gcggtgcgat ga                           1062

<210> SEQ ID NO 4
<211> LENGTH: 353
<212> TYPE: PRT
<213> ORGANISM: Synechococcus sp.
```

<400> SEQUENCE: 4

```
Met Arg Thr Leu Leu Ser Ala Phe Ser Leu Thr Ala Leu Thr Val Gly
 1               5                  10                  15

Phe Leu Thr Ala Thr Ser Ala Gln Ala Gln Thr Val Gln Ile Ser Gly
            20                  25                  30

Ala Gly Ala Thr Phe Ala Ala Pro Leu Leu Gln Arg Trp Phe Asp Ala
        35                  40                  45

Tyr Asn Arg Thr Val Asp Pro Thr Val Gln Val Ser Tyr Gln Ser Val
    50                  55                  60

Gly Ser Gly Ala Gly Leu Glu Gln Val Ile Asn Gly Thr Val Asp Phe
65                  70                  75                  80

Gly Ala Ser Glu Ala Pro Phe Ser Gly Ala Arg Leu Glu Ser Phe Arg
                85                  90                  95

Ala Lys Tyr Gly Tyr Asp Pro Leu Gln Leu Pro Leu Ala Gly Gly Ala
            100                 105                 110

Ile Glu Phe Ala Tyr Asn Leu Pro Gly Ile Glu Asp Gly Glu Leu Ile
        115                 120                 125

Leu Lys Arg Lys Thr Tyr Cys Gly Ile Val Thr Gly Glu Ile Thr Arg
130                 135                 140

Trp Asp Asp Ile Arg Ile Lys Ala Glu Asn Pro Gly Ile Ala Asn Lys
145                 150                 155                 160

Leu Pro Pro Leu Asp Ile Thr Trp Val His Arg Ser Asp Gly Ser Gly
                165                 170                 175

Thr Thr Phe Val Phe Thr Asn His Ile Arg Thr Val Cys Pro Asn Trp
            180                 185                 190

Thr Ala Gly Ala Gly Thr Ser Val Glu Trp Pro Val Gly Ile Gly Ala
        195                 200                 205

Gln Gly Asn Glu Gly Val Ala Ala Thr Ile Lys Gln Glu Pro Gly Ala
    210                 215                 220

Ile Gly Tyr Val Asn Gln Ser Tyr Ala Lys Leu Glu Lys Met Ala Thr
225                 230                 235                 240

Ala Arg Leu Glu Asn Lys Ala Gly Asn Ile Val Glu Phe Ser Thr Glu
                245                 250                 255

Ala Ala Thr Ser Ala Leu Asp Ala Pro Ile Pro Asp Asp Phe Ala Leu
            260                 265                 270

Leu Val Pro Asp Pro Glu Gly Pro Asn Asp Tyr Pro Ile Val Gly Leu
        275                 280                 285

Phe Trp Val Met Leu Tyr Arg Glu Tyr Pro Asp Gln Gln Lys Leu Thr
    290                 295                 300

Lys Leu Val Glu Ala Leu Lys Trp Thr Gln Gly Pro Glu Gly Gln Ala
305                 310                 315                 320

Ile Thr Lys Glu Leu Asp Tyr Ile Pro Met Pro Glu Ala Val Ile Gln
                325                 330                 335

Arg Ile Phe Ala Glu Leu Asp Ser Ile Thr Val Asn Pro Asn Ala Val
            340                 345                 350

Arg
```

<210> SEQ ID NO 5
<211> LENGTH: 2421
<212> TYPE: DNA
<213> ORGANISM: Artificial Sequence
<220> FEATURE:
<223> OTHER INFORMATION: DNA sequence of phosphate biosensor gene

<400> SEQUENCE: 5

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgacctg gggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg ccaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc ggtaccgtag gatttctaac agcgacctcg     720
gctcaagccc aaaccgtgca aatctccggg gcgggcgcga cctttgcggc tcctttgctg     780
caacgttggt ttgacgccta caaccgcacc gtagacccca ctgtgcaagt cagctatcag     840
tctgtcggta gtggtgctgg cctagagcag gtgatcaatg gcactgtgga cttcggcgct     900
tccgaggcgc ctttctccgg tgctcgcctg gaaagcttcc gagctaaata cggctatgat     960
cccctacagt tgcctctggc gggagggggcc atcgagtttg cctataacct gcccggcatt    1020
gaagacggag agctcatcct gaagcggaaa acctactgcg catcgtgac cggcgagatc     1080
actcgctggg acgacattcg catcaaggcc gagaacccag gtatagcaaa caagctgcca    1140
cccctggaca tcacctgggt acaccgctct gatggttctg ggactacctt tgtgttcacc    1200
aaccacatca gaactgtctg ccctaattgg acagccggtg ctggtacttc tgtcgagtgg    1260
cctgttggta ttggagccca agggaatgag ggcgtagccg ccaccatcaa gcaggagcca    1320
ggggcgattg gctacgtgaa ccagtcctat gccaagctgg aaaagatggc cactgctcgc    1380
ttggaaaaca aagcgggcaa cattgttgag ttctcgactg aggcagctac ctcggcgctg    1440
gatgctccca ttcctgatga cttttgcgctg ttggtgcccg accctgaagg gccaaatgac    1500
tacccaatcg tgggcttgtt ctgggtgatg ctgtaccgcg agtatcccga tcagcagaag    1560
ctgaccaagc tggtggaggc tctgaagtgg acccaggggc cagagggtca agccatcacc    1620
aaggagctgg actacatccc tatgcctgag gcggttatcc agcggatctt tgcagagctg    1680
gattccatca ccgttaacgg taccgtgagc aagggcgagg agctgttcac cggggtggtg    1740
cccatcctgg tcgagctgga cggcgacgta aacggccaca gttcagcgt gtccggcgag    1800
ggcgagggcg atgccaccta cggcaagctg accctgaagt tcatctgcac caccggcaag    1860
ctgcccgtgc cctggcccac cctcgtgacc accttcggct acggcctgca gtgcttcgcc    1920
cgctaccccg accacatgaa gcagcacgac ttcttcaagt ccgccatgcc cgaaggctac    1980
gtccaggagc gcaccatctt cttcaaggac gacggcaact acaagacccg cgccgaggtg    2040
aagttcgagg gcgacaccct ggtgaaccgc atcgagctga agggcatcga cttcaaggag    2100
gacggcaaca tcctggggca caagctggag tacaactaca cagccacaa cgtctatatc    2160
atggccgaca agcagaagaa cggcatcaag gtgaacttca agatccgcca caacatcgag    2220
gacggcagcg tgcagctcgc cgaccactac cagcagaaca cccccatcgg cgacggcccc    2280
gtgctgctgc ccgacaacca ctacctgagc taccagtccg ccctgagcaa agaccccaac    2340
```

-continued

```
gagaagcgcg atcacatggt cctgctggag ttcgtgaccg ccgccgggat cactctcggc   2400
atggacgagc tgtacaagta a                                             2421
```

<210> SEQ ID NO 6
<211> LENGTH: 806
<212> TYPE: PRT
<213> ORGANISM: Artificial Sequence
<220> FEATURE:
<223> OTHER INFORMATION: Protein sequence of phosphate biosensor gene

<400> SEQUENCE: 6

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Gly Thr Val Gly Phe Leu Thr Ala Thr Ser
225                 230                 235                 240

Ala Gln Ala Gln Thr Val Gln Ile Ser Gly Ala Gly Ala Thr Phe Ala
                245                 250                 255

Ala Pro Leu Leu Gln Arg Trp Phe Asp Ala Tyr Asn Arg Thr Val Asp
            260                 265                 270

Pro Thr Val Gln Val Ser Tyr Gln Ser Val Gly Ser Gly Ala Gly Leu
        275                 280                 285

Glu Gln Val Ile Asn Gly Thr Val Asp Phe Gly Ala Ser Glu Ala Pro
290                 295                 300

Phe Ser Gly Ala Arg Leu Glu Ser Phe Arg Ala Lys Tyr Gly Tyr Asp
305                 310                 315                 320

Pro Leu Gln Leu Pro Leu Ala Gly Gly Ala Ile Glu Phe Ala Tyr Asn
                325                 330                 335

Leu Pro Gly Ile Glu Asp Gly Glu Leu Ile Leu Lys Arg Lys Thr Tyr
```

```
              340                 345                 350
Cys Gly Ile Val Thr Gly Glu Ile Thr Arg Trp Asp Asp Ile Arg Ile
            355                 360                 365
Lys Ala Glu Asn Pro Gly Ile Ala Asn Lys Leu Pro Pro Leu Asp Ile
370                 375                 380
Thr Trp Val His Arg Ser Asp Gly Ser Gly Thr Phe Val Phe Thr
385                 390                 395                 400
Asn His Ile Arg Thr Val Cys Pro Asn Trp Thr Ala Gly Ala Gly Thr
                405                 410                 415
Ser Val Glu Trp Pro Val Gly Ile Gly Ala Gln Gly Asn Glu Gly Val
            420                 425                 430
Ala Ala Thr Ile Lys Gln Glu Pro Gly Ala Ile Gly Tyr Val Asn Gln
        435                 440                 445
Ser Tyr Ala Lys Leu Glu Lys Met Ala Thr Ala Arg Leu Glu Asn Lys
    450                 455                 460
Ala Gly Asn Ile Val Glu Phe Ser Thr Glu Ala Ala Thr Ser Ala Leu
465                 470                 475                 480
Asp Ala Pro Ile Pro Asp Asp Phe Ala Leu Leu Val Pro Asp Pro Glu
                485                 490                 495
Gly Pro Asn Asp Tyr Pro Ile Val Gly Leu Phe Trp Val Met Leu Tyr
            500                 505                 510
Arg Glu Tyr Pro Asp Gln Gln Lys Leu Thr Lys Leu Val Glu Ala Leu
        515                 520                 525
Lys Trp Thr Gln Gly Pro Glu Gly Gln Ala Ile Thr Lys Glu Leu Asp
    530                 535                 540
Tyr Ile Pro Met Pro Glu Ala Val Ile Gln Arg Ile Phe Ala Glu Leu
545                 550                 555                 560
Asp Ser Ile Thr Val Asn Gly Thr Val Ser Lys Gly Glu Glu Leu Phe
                565                 570                 575
Thr Gly Val Val Pro Ile Leu Val Glu Leu Asp Gly Asp Val Asn Gly
            580                 585                 590
His Lys Phe Ser Val Ser Gly Glu Gly Glu Gly Asp Ala Thr Tyr Gly
        595                 600                 605
Lys Leu Thr Leu Lys Phe Ile Cys Thr Thr Gly Lys Leu Pro Val Pro
    610                 615                 620
Trp Pro Thr Leu Val Thr Thr Phe Gly Tyr Gly Leu Gln Cys Phe Ala
625                 630                 635                 640
Arg Tyr Pro Asp His Met Lys Gln His Asp Phe Phe Lys Ser Ala Met
                645                 650                 655
Pro Glu Gly Tyr Val Gln Glu Arg Thr Ile Phe Phe Lys Asp Asp Gly
            660                 665                 670
Asn Tyr Lys Thr Arg Ala Glu Val Lys Phe Glu Gly Asp Thr Leu Val
        675                 680                 685
Asn Arg Ile Glu Leu Lys Gly Ile Asp Phe Lys Glu Asp Gly Asn Ile
    690                 695                 700
Leu Gly His Lys Leu Glu Tyr Asn Tyr Asn Ser His Asn Val Tyr Ile
705                 710                 715                 720
Met Ala Asp Lys Gln Lys Asn Gly Ile Lys Val Asn Phe Lys Ile Arg
                725                 730                 735
His Asn Ile Glu Asp Gly Ser Val Gln Leu Ala Asp His Tyr Gln Gln
            740                 745                 750
Asn Thr Pro Ile Gly Asp Gly Pro Val Leu Leu Pro Asp Asn His Tyr
        755                 760                 765
```

```
Leu Ser Tyr Gln Ser Ala Leu Ser Lys Asp Pro Asn Glu Lys Arg Asp
            770             775             780

His Met Val Leu Leu Glu Phe Val Thr Ala Ala Gly Ile Thr Leu Gly
785             790             795             800

Met Asp Glu Leu Tyr Lys
                805
```

NUCLEIC ACIDS ENCODING PHOSPHATE FLUORESCENT INDICATORS AND METHODS OF USING THE SAME

STATEMENT OF GOVERNMENT SUPPORT

This work was supported by Human Frontier Science Program grant No. RGP0041/2004C. The government may have certain rights to this invention.

RELATED APPLICATIONS

The present application is a U.S. National Phase Application of International Application No. PCT/US2005/036955, filed Oct. 14, 2005, which is incorporated herein in its entirety.

FIELD OF INVENTION

The invention relates generally to the construction of phosphate biosensors and methods for measuring and detecting changes in phosphate levels using fluorescence resonance energy transfer (FRET).

BACKGROUND OF INVENTION

All publications and patent applications herein are incorporated by reference to the same extent as if each individual publication or patent application was specifically and individually indicated to be incorporated by reference.

The publications discussed herein are provided solely for their disclosure prior to the filing date of the present application. Nothing herein is to be construed as an admission that the present invention is not entitled to antedate such publication by virtue of prior invention.

Phosphate (Pi) is an essential macronutrient for all living organisms. It is involved in most metabolic and signaling events in a cell, and is present in multiple cellular compartments. It serves various basic biological functions as a structural element in nucleic acids, phospholipids and ATP, as a metabolite involved in energy transfer, as a component in signal transduction cascades, and in the regulation of enzymes and metabolic processes.

Adenosine triphosphate (ATP) is the dominant 'energy currency' in the cell. The hydrolysis of ATP to adenosine diphosphate (ADP) plus Pi releases energy that fuels enumerable energy-requiring processes in the cell. Indeed, ATP is required for the phosphorylation of glucose (to generate glucose 6-phosphate), which enables glucose to enter the glycolytic pathway. Complete aerobic oxidation of a single glucose 6-phosphate molecule yields 30-36 molecules of ATP. Therefore, Pi is a critical metabolite and an essential nutrient, and the concentration of this molecule can profoundly alter cellular growth and metabolism. It is surprising, then, how little is known about the subcellular distribution phosphate and homeostasis under different phosphate concentrations.

To be able to measure phosphate levels directly in living cells, it would be useful to have a nanosensor for phosphate. A phosphate sensor would be an excellent tool for discovery and drug screening. The response of phosphate levels could be measured in real time in response to chemicals, metabolic events, transport steps, and signaling processes.

Recently a number of bacterial periplasmic binding proteins (PBP), which undergo a venus flytrap-like closure of two lobes upon substrate binding, have been successfully used as the scaffold of metabolite nanosensors (Fehr, M., Frommer, W. B., and Lalonde, S. (2002) Visualization of maltose uptake in living yeast cells by fluorescent nanosensors. Proc. Natl. Acad. Sci. USA 99, 9846-9851; Fehr, M., Lalonde, S., Lager, I., Wolff, M. W., and Frommer, W. B. (2003) In vivo imaging of the dynamics of glucose uptake in the cytosol of COS-7 cells by fluorescent nanosensors. J. Biol. Chem. 278, 19127-19133; Lager, I., Fehr, M., Frommer, W. B., and Lalonde, S. (2003) Development of a fluorescent nanosensor for ribose. FEBS Lett 553, 85-89). The PBP nanosensors thus far developed have been constructed using type I periplasmic binding proteins, wherein the fluorophores attached to the N- and C-termini of the protein are located on two different lobes.

There is a PBP for phosphate (PiBP) that has been isolated from various gram negative bacteria. For instance, the synthesis of the PiBP, the product of the pstS gene, is induced in E. coli when cell growth is limited by low Pi availability. However, in contrast to the type I PBPs used for nanosensors thus far, periplasmic phosphate binding protein has been classified as a type II PBP, with N- and C-termini located on the same protein lobe (Tam, R., and Saier, M. H. (1993) Microbiol Rev 57(2), 320-346; Fukami-Kobayashi, K., Tateno, Y., and Nishikawa, K. (1999) J Mol Biol 286(1), 279-290). The crystal structure of phosphate binding protein has been studied, and the modeled structures of PiBP also suggest a type II configuration although the assignment of both N- and C-terminal region is uncertain (Hirshberg, M., Henrick, K., Haire, L. L., Vasisht, N., Brune, M., Corrie, J. E. T., and Webb, M. R. (1998) Biochemistry-Us 37(29), 10381-10385; Ledvina, P. S., Tsai, A. L., Wang, Z. M., Koehl, E., and Quiocho, F. A. (1998) Protein Sci 7(12), 2550-2559). In addition, phosphate quenches fluorescence, making the analysis of phosphate sensors potentially problematic. Therefore, it was not clear whether a phosphate PBP sensor could be generated using the strategies employed for type I PBP sensors.

SUMMARY OF INVENTION

The present inventors have surprisingly found that periplasmic phosphate binding proteins may be used to construct biosensors for phosphate. The present invention thus provides phosphate biosensors that may be used for detecting and measuring changes in phosphate concentrations in living cells. In particular, the invention provides an isolated nucleic acid which encodes a phosphate fluorescent indicator, the indicator comprising a phosphate binding protein moiety, a donor fluorescent protein moiety covalently coupled to the phosphate binding protein moiety, and an acceptor fluorescent protein moiety covalently coupled to the phosphate binding protein moiety, wherein fluorescence resonance energy transfer (FRET) between the donor moiety and the acceptor moiety is altered when the donor moiety is excited and phosphate binds to the phosphate binding protein moiety. Vectors, including expression vectors, and host cells comprising the inventive nucleic acids are also provided, as well as biosensor proteins encoded by the nucleic acids. Such nucleic acids, vectors, host cells and proteins may be used in methods of detecting phosphate binding and changes in levels of phosphate, and in methods of identifying compounds that modulate phosphate binding or phosphate-mediated activities.

DETAILED DESCRIPTION OF INVENTION

The following description includes information that may be useful in understanding the present invention. It is not an admission that any of the information provided herein is prior art or relevant to the presently claimed inventions, or that any publication specifically or implicitly referenced is prior art.

Other objects, advantages and features of the present invention become apparent to one skilled in the art upon reviewing the specification and the drawings provided herein. Thus, further objects and advantages of the present invention will be clear from the description that follows.

Periplasmic Phosphate Binding Protein (PiBP)

The uptake of Pi into gram negative bacteria is initiated by the binding of this anion to a periplasmically-localized, Pi-binding protein (PiBP). There are more than 20 known analogous binding proteins that function in the uptake of sugars, oxyanions, amino acids, and oligopeptides. The synthesis of the PiBP, the product of the pstS gene, is induced in *E. coli* when cell growth is limited by low Pi availability. PiBP exhibits specific binding to both monobasic ($H_2PO_4^-$) and dibasic ($HPO_4^{2-}$) phosphate (Wang, Z. M., Choudhary, A., Ledvina, P. S., and Quiocho, F. A. (1994) *J Biol Chem* 269(40), 25091-25094), with a $K_d$ of 0.8 nM (Medveczky, N., and Rosenberg, H. (1970) *Biochim Biophys Acta* 211(2), 158). The dissociation rate constant is 21 $s^{-1}$ at pH 7.0 and low ionic strength (Brune, M., Hunter, J. L., Corrie, J. E. T., and Webb, M. R. (1994) *Biochemistry-Us* 33(27), 8262-8271).

The PiBP consists of two globular domains connected by peptide segments that create a flexible hinge (Ledvina, P. S., Yao, N. H., Choudhary, A., and Quiocho, F. A. (1996) *P Natl Acad Sci USA* 93(13), 6786-6791). In the absence of Pi, the globular domains are separated, exposing a cleft that is accessible to soluble metabolites. A conformational change in the protein occurs upon binding of Pi, whereupon the globular domains come closer together, the binding of Pi becomes tighter as a consequence of hydrogen bonding of the Pi to amino acids of the cleft (Luecke, H., and Quiocho, F. A. (1990) *Nature* 347(6291), 402-406), and the binding pocket becomes inaccessible to the solvent environment. As discussed above, PiBP has been classified as a type II PBP wherein the N- and C-termini are located on the same lobe of the protein.

Figure 7:
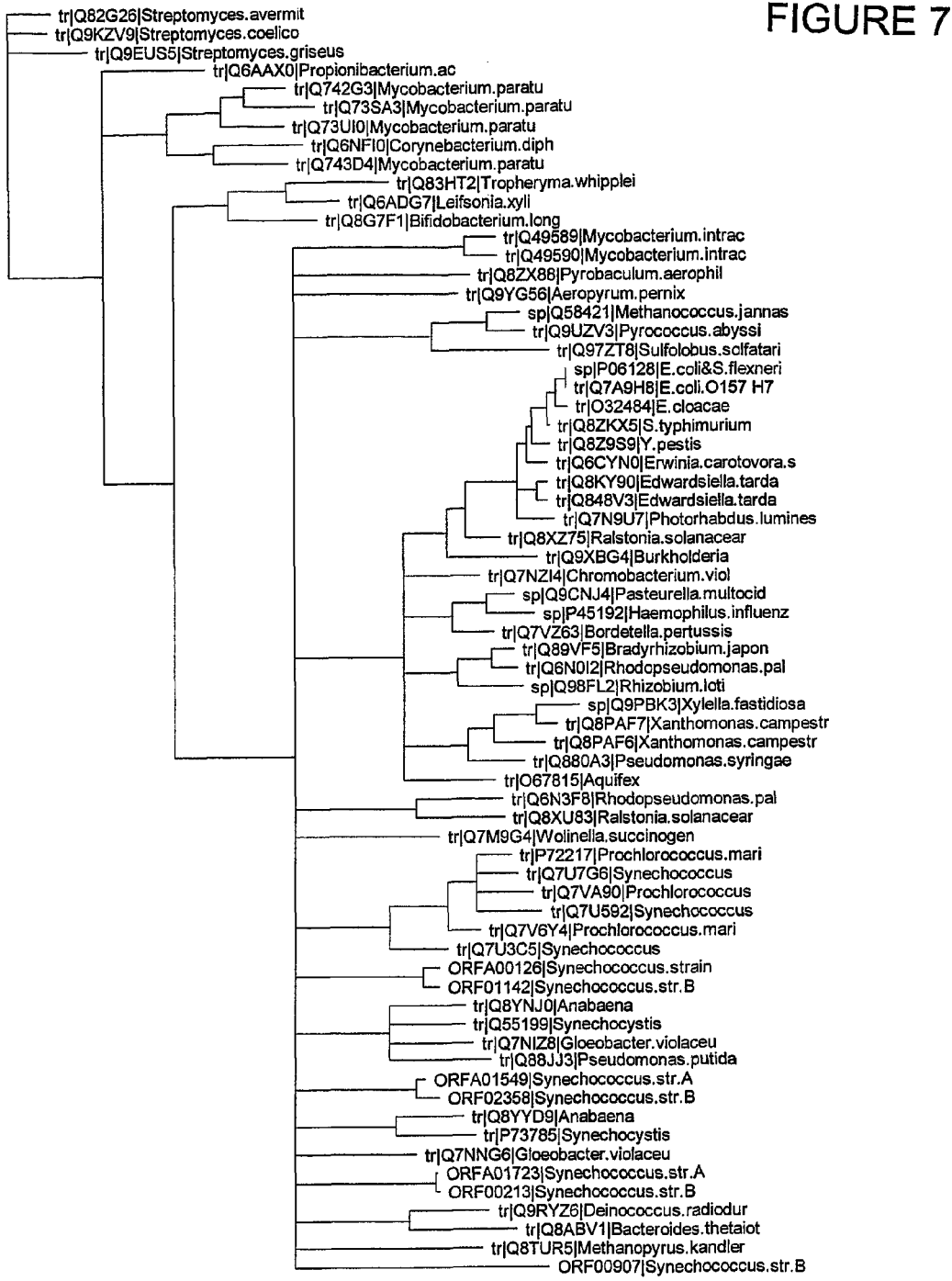
FIG. 7 shows a phylogenic tree made by PAUP showing the relationship between PiBP proteins of various species.

PiBP DNA sequences may be obtained from public databases, for instance the NCBI website, or cloned from any Gram negative bacterium of interest using techniques that are well known in the art. Cyanobacteria are a good source for PiBP sequences, as are thermophilic and hyperthermophilic bacteria, since the proteins isolated from these bacteria display enhanced stability under conditions of extreme temperature, pH or chemical exposure. See Application Ser. No. 60/658,142, which is herein incorporated by reference in its entirety. A phylogenic tree made by PAUP, showing the relationship between PiBP sequences of various species, is shown in FIG. 7.

For instance, to exemplify the present invention, a truncated PiBP (protein accession NP_415188), encoding the encoding the predicted mature protein without the signal sequence, was amplified by PCR from a thermophilic strain of *Synechococcus* isolated from the hot springs of Yellowstone National Park. The sequence was amplified from genomic DNA using the primers 5'-ATTGGTACCGTAG-GATTTCTAACAGCG-3' (SEQ ID NO: 1) and 5'-ATAGG-TACCGTTAACGGTGATGGAATC-3' (SEQ ID NO: 2), and has the sequence of SEQ ID NO: 3 including the signal sequence. The sequence of the *Synechococcus* sp. PiBP is 36.9% identical to PiBP of *E. coli* (encoded by pstS: PDB 1a40) (De Lorimier, R. M., Smith, J. J., Dwyer, M. A., Looger, L. L., Sali, K. M., Paavola, C. D., Rizk, S. S., Sadigov, S., Conrad, D. W., Loew, L., and Hellinga, H. W. (2002) *Protein Sci* 11(11), 2655-2675), with the two proteins having a very similar predicted tertiary structure (see FIG. 1).

Biosensors

The present invention provides phosphate biosensors for detecting and measuring changes in phosphate concentrations using Fluorescence Resonance Energy Transfer (FRET). The term "phosphate" includes both monobasic ($H_2PO_4^-$) and dibasic ($HPO_4^{2-}$) phosphate, and all other forms of phosphate for which a receptor exists.

In particular, the invention provides isolated nucleic acids encoding phosphate binding fluorescent indicators and the phosphate fluorescent indicators encoded thereby. One embodiment, among others, is an isolated nucleic acid which encodes a phosphate binding fluorescent indicator, the indicator comprising: a phosphate binding protein moiety, a donor fluorescent protein moiety covalently coupled to the phosphate binding protein moiety, and an acceptor fluorescent protein moiety covalently coupled to the phosphate binding protein moiety, wherein FRET between the donor moiety and the acceptor moiety is altered when the donor moiety is excited and phosphate binds to the phosphate binding protein moiety.

As used herein, "covalently coupled" means that the donor and acceptor fluorescent moieties may be conjugated to the ligand binding protein moiety via a chemical linkage, for instance to a selected amino acid in said ligand binding protein moiety. Covalently coupled also means that the donor and acceptor moieties may be genetically fused to the ligand binding protein moiety such that the ligand binding protein moiety is expressed as a fusion protein comprising the donor and acceptor moieties. As described herein, the donor and acceptor moieties may be fused to the tennini of the phosphate binding moiety or to an internal position within the phosphate binding moiety so long as FRET between the donor moiety and the acceptor moiety is altered when the donor moiety is excited and phosphate binds to the phosphate binding protein moiety.

A preferred phosphate binding protein moiety, among others, is a phosphate binding protein moiety from the *Synechococcus* PiBP protein having the sequence of SEQ ID NO: 4. Any portion of the PiBP DNA sequence which encodes a phosphate binding region may be used in the nucleic acids of the present invention. Phosphate binding portions of PiBP or any of its homologues from other organisms, for instance Gram negative bacteria including thermophilic and hyperthermophilic organisms, may be cloned into the vectors described herein and screened for activity according to the disclosed assays.

Naturally occurring species variants of PiBP may also be used, in addition to artificially engineered variants comprising site-specific mutations, deletions or insertions that maintain measurable phosphate binding function. Variant nucleic acid sequences suitable for use in the nucleic acid constructs of the present invention will preferably have at least 30, 40, 50, 60, 70, 75, 80, 85, 90, 95, or 99% similarity or identity to the gene sequence for PiBP. Suitable variant nucleic acid sequences may also hybridize to the gene for PiBP under highly stringent hybridization conditions. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993), which is herein incorporated by reference. Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

Preferred artificial variants of the present invention may be designed to exhibit decreased affinity for the ligand, in order to expand the range of ligand concentration that can be measured by the disclosed nanosensors. Additional artificial variants showing decreased or increased binding affinity for ligands may be constructed by random or site-directed mutagenesis and other known mutagenesis techniques, and cloned into the vectors described herein and screened for activity according to the disclosed assays. The binding specificity of disclosed biosensors may also be altered by mutagenesis so as to alter the ligand recognized by the biosensor. See, for instance, Looger et al., Nature, 423 (6936): 185-190. Due to the similarity of sulfate and phosphate PBPs, it may also be possible to create a phosphate binding protein from a sulfate binding protein using site-directed mutagenesis.

The sensors of the invention may also be designed with a phosphate binding moiety and one or more additional protein binding moieties that are covalently coupled or fused together and to the donor and acceptor fluorescent moieties in order to generate an allosteric enzyme whose activity is controlled by more than one ligand. Allosteric enzymes containing dual specificity for more than one ligand have been described in the art, and may be used to construct the FRET biosensors described herein (Guntas and Ostermeier, 2004, J. Mol. Biol. 336(1): 263-73).

The isolated nucleic acids of the invention may incorporate any suitable donor and acceptor fluorescent protein moieties that are capable in combination of serving as donor and acceptor moieties in FRET. Preferred donor and acceptor moieties are selected from the group consisting of GFP (green fluorescent protein), CFP (cyan fluorescent protein), BFP (blue fluorescent protein), YFP (yellow fluorescent protein), and enhanced variants thereof, with a particularly preferred embodiment provided by the donor/acceptor pair CFP/YFP Venus, a variant of YFP with improved pH tolerance and maturation time (Nagai, T., Ibata, K., Park, E. S., Kubota, M., Mikoshiba, K., and Miyawaki, A. (2002) A variant of yellow fluorescent protein with fast and efficient maturation for cell-biological applications. Nat. Biotechnol. 20, 87-90). An alternative is the MiCy/mKO pair with higher pH stability and a larger spectral separation (Karasawa S, Araki T, Nagai T, Mizuno H, Miyawaki A. Cyan-emitting and orange-emitting fluorescent proteins as a donor/acceptor pair for fluorescence resonance energy transfer. Biochem J. 2004 381:307-12). Also suitable as either a donor or acceptor is native DsRed from a Discosoma species, an ortholog of DsRed from another genus, or a variant of a native DsRed with optimized properties (e.g. a K83M variant or DsRed2 (available from Clontech)). Criteria to consider when selecting donor and acceptor fluorescent moieties is known in the art, for instance as disclosed in U.S. Pat. No. 6,197,928, which is herein incorporated by reference in its entirety.

As used herein, the term "variant" is intended to refer to polypeptides with at least about 30%, 40%, 50%, 60%, 70%, more preferably at least 75% identity, including at least 80%, 90%, 95% or greater identity to native fluorescent molecules. Many such variants are known in the art, or can be readily prepared by random or directed mutagenesis of a native fluorescent molecules (see, for example, Fradkov et al., FEBS Lett. 479:127-130 (2000)).

When the fluorophores of the biosensor contain stretches of similar or related sequence(s), the present inventors have recently discovered that gene silencing may adversely affect expression of the biosensor in certain cells and particularly whole organisms. In such instances, it is possible to modify the fluorophore coding sequences at one or more degenerate or wobble positions of the codons of each fluorophore, such that the nucleic acid sequences of the fluorophores are modified but not the encoded amino acid sequences. Alternative, one or more conservative substitutions that do not adversely affect the function of the fluorophores may also be incorporated. See PCT application PCT/US2005/036953, "Methods of Reducing Repeat-Induced Silencing of Transgene Expression and Improved Fluorescent Biosensors", which is herein incorporated by reference in its entirety.

It is also possible to use or luminescent quantum dots (QD) for FRET (Clapp et al., 2005, J. Am. Chem. Soc. 127(4): 1242-50), dyes, including but not limited to TOTO dyes (Laib and Seeger, 2004, J. Fluoresc. 14(2):187-91), Cy3 and Cy5

(Churchman et al., 2005, Proc Natl Acad Sci USA. 102(5): 1419-23), Texas Red, fluorescein, and tetramethylrhodamine (TAMRA) (Unruh et al., Photochem Photobiol. 2004 Oct. 1), AlexaFluor 488, to name a few, as well as fluorescent tags (see, for example, Hoffman et al., 2005, Nat. Methods 2(3): 171-76).

The invention further provides vectors containing isolated nucleic acid molecules encoding the biosensor polypeptides described herein. Exemplary vectors include vectors derived from a virus, such as a bacteriophage, a baculovirus or a retrovirus, and vectors derived from bacteria or a combination of bacterial sequences and sequences from other organisms, such as a cosmid or a plasmid. Such vectors include expression vectors containing expression control sequences operatively linked to the nucleic acid sequence coding for the biosensor. Vectors may be adapted for function in a prokaryotic cell, such as *E. coli* or other bacteria, or a eukaryotic cell, including animal cells or plant cells. For instance, the vectors of the invention will generally contain elements such as an origin of replication compatible with the intended host cells, one or more selectable markers compatible with the intended host cells and one or more multiple cloning sites. The choice of particular elements to include in a vector will depend on factors such as the intended host cells, the insert size, whether regulated expression of the inserted sequence is desired, i.e., for instance through the use of an inducible or regulatable promoter, the desired copy number of the vector, the desired selection system, and the like. The factors involved in ensuring compatibility between a host cell and a vector for different applications are well known in the art.

Preferred vectors for use in the present invention will permit cloning of the phosphate binding domain or receptor between nucleic acids encoding donor and acceptor fluorescent molecules, resulting in expression of a chimeric or fusion protein comprising the phosphate binding domain covalently coupled to donor and acceptor fluorescent molecules. Exemplary vectors include the bacterial pRSET-FLIP derivatives disclosed in Fehr et al. (2002) (Visualization of maltose uptake in living yeast cells by fluorescent nanosensors, Proc. Natl. Acad. Sci. USA 99, 9846-9851), which is herein incorporated by reference in its entirety. Methods of cloning nucleic acids into vectors in the correct frame so as to express a fusion protein are well known in the art.

The phosphate biosensors of the present invention may be expressed in any location in the cell, including the cytoplasm, cell surface or subcellular organelles such as the nucleus, vesicles, ER, vacuole, etc. Methods and vector components for targeting the expression of proteins to different cellular compartments are well known in the art, with the choice dependent on the particular cell or organism in which the biosensor is expressed. See, for instance, Okumoto, S., Looger, L. L., Micheva, K. D., Reimer, R. J., Smith, S. J., and Frommer, W. B. (2005) *P Natl Acad Sci USA* 102(24), 8740-8745; Fehr, M., Lalonde, S., Ehrhardt, D. W., and Frommer, W. B. (2004) *J Fluoresc* 14(5), 603-609, which are herein incorporated by reference in their entireties.

The chimeric nucleic acids of the present invention may be constructed such that the donor and acceptor fluorescent moiety coding sequences are fused to separate termini of the ligand binding domain in a manner such that changes in FRET between donor and acceptor may be detected upon ligand binding. Fluorescent domains can optionally be separated from the ligand binding domain by one or more flexible linker sequences. Such linker moieties are preferably between about 1 and 50 amino acid residues in length, and more preferably between about 1 and 30 amino acid residues. Linker moieties and their applications are well known in the art and described, for example, in U.S. Pat. Nos. 5,998,204 and 5,981,200, and Newton et al., Biochemistry 35:545-553 (1996). Alternatively, shortened versions of linkers or any of the fluorophores described herein may be used. For example, the inventors have shown that deleting N- or C-terminal portions of any of the three modules can lead to increased FRET ratio changes, as described in Application Ser. No. 60/658,141, which is herein incorporated by reference in its entirety.

It will also be possible depending on the nature and size of the phosphate binding domain to insert one or both of the fluorescent molecule coding sequences within the open reading frame of the phosphate binding protein such that the fluorescent moieties are expressed and displayed from a location within the biosensor rather than at the termini. Such sensors are generally described in U.S. Application Ser. No. 60/658,141, which is herein incorporated by reference in its entirety. It will also be possible to insert a phosphate binding sequence into a single fluorophore coding sequence, i.e. a sequence encoding a GFP, YFP, CFP, BFP, etc., rather than between tandem molecules. According to the disclosures of U.S. Pat. Nos. 6,469,154 and 6,783,958, each of which is incorporated herein by reference in their entirety, such sensors respond by producing detectable changes within the protein that influence the activity of the fluorophore.

The invention also includes host cells transfected with a vector or an expression vector of the invention, including prokaryotic cells, such as *E. coli* or other bacteria, or eukaryotic cells, such as yeast cells, animal cells or plant cells. In another aspect, the invention features a transgenic non-human animal having a phenotype characterized by expression of the nucleic acid sequence coding for the expression of the environmentally stable biosensor. The phenotype is conferred by a transgene contained in the somatic and germ cells of the animal, which may be produced by (a) introducing a transgene into a zygote of an animal, the transgene comprising a DNA construct encoding the phosphate biosensor; (b) transplanting the zygote into a pseudopregnant animal; (c) allowing the zygote to develop to term; and (d) identifying at least one transgenic offspring containing the transgene. The step of introducing of the transgene into the embryo can be achieved by introducing an embryonic stem cell containing the transgene into the embryo, or infecting the embryo with a retrovirus containing the transgene. Transgenic animals of the invention include transgenic *C. elegans* and transgenic mice and other animals. Transgenic plants are also included.

The present invention also encompasses isolated phosphate biosensor molecules having the properties described herein, particularly phosphate binding fluorescent indicators constructed using hyperthermophilic and moderately thermophilic proteins. Such polypeptides may be recombinantly expressed using the nucleic acid constructs described herein, or produced by chemically coupling some or all of the component domains. The expressed polypeptides can optionally be produced in and/or isolated from a transcription-translation system or from a recombinant cell, by biochemical and/or immunological purification methods known in the art. The polypeptides of the invention can be introduced into a lipid bilayer, such as a cellular membrane extract, or an artificial lipid bilayer (e.g. a liposome vesicle) or nanoparticle.

Methods of Detecting Phosphate

The nucleic acids and proteins of the present invention are useful for detecting phosphate binding and measuring changes in the levels of phosphate both in vitro and in a plant or an animal. In one embodiment, the invention comprises a method of detecting changes in the level of phosphate in a sample of cells, comprising (a) providing a cell expressing a nucleic acid encoding a phosphate biosensor as described herein and a sample of cells; and (b) detecting a change in FRET between a donor fluorescent protein moiety and an acceptor fluorescent protein moiety, each covalently attached to the phosphate binding domain, wherein a change in FRET between said donor moiety and said acceptor moiety indicates a change in the level of phosphate in the sample of cells.

FRET may be measured using a variety of techniques known in the art. For instance, the step of determining FRET may comprise measuring light emitted from the acceptor fluorescent protein moiety. Alternatively, the step of determining FRET may comprise measuring light emitted from the donor fluorescent protein moiety, measuring light emitted from the acceptor fluorescent protein moiety, and calculating a ratio of the light emitted from the donor fluorescent protein moiety and the light emitted from the acceptor fluorescent protein moiety. The step of determining FRET may also comprise measuring the excited state lifetime of the donor moiety or anisotropy changes (Squire A, Verveer P J, Rocks O, Bastiaens P I. J Struct Biol. 2004 July; 147(1):62-9. Red-edge anisotropy microscopy enables dynamic imaging of homo-FRET between green fluorescent proteins in cells.). Such methods are known in the art and described generally in U.S. Pat. No. 6,197,928, which is herein incorporated by reference in its entirety.

The amount of phosphate in a sample of cells can be determined by determining the degree of FRET. First the sensor must be introduced into the sample. Changes in phosphate concentration can be determined by monitoring FRET at a first and second time after contact between the sample and the fluorescent indicator and determining the difference in the degree of FRET. The amount of phosphate in the sample can be quantified for example by using a calibration curve established by titration.

The cell sample to be analyzed by the methods of the invention may be contained in vivo, for instance in the measurement of phosphate transport or signaling on the surface of cells, or in vitro, wherein phosphate efflux may be measured in cell culture. Alternatively, a fluid extract from cells or tissues may be used as a sample from which phosphate is detected or measured.

Methods for detecting phosphate levels as disclosed herein may be used to screen and identify compounds that may be used to modulate phosphate concentrations and activities relating to phosphate changes. In one embodiment, among others, the invention comprises a method of identifying a compound that modulates phosphate binding or levels comprising (a) contacting a mixture comprising a cell expressing an phosphate biosensor as disclosed herein and a sample of cells with one or more test compounds, and (b) determining FRET between said donor fluorescent domain and said acceptor fluorescent domain following said contacting, wherein increased or decreased FRET following said contacting indicates that said test compound is a compound that modulates phosphate binding activity or phosphate levels.

The term "modulate" in this embodiment means that such compounds may increase or decrease phosphate binding activity, or may affect activities, i.e., cell functions or signaling cascades, that affect phosphate levels. Compounds that increase or decrease phosphate binding activity may be targets for therapeutic intervention and treatment of disorders associated with aberrant phosphate activity, or with aberrant cell metabolism or signal transduction, as described above. Other compounds that increase or decrease phosphate binding activity or phosphate levels associated with cellular functions may be developed into therapeutic products for the treatment of disorders associated with ligand binding activity.

Utilities

The phosphate sensors of the present invention will be useful for a wide range of applications, e.g. to study phosphate levels in marine systems with better precision. New tools for such measurements are required since the marine biogeochemical phosphorus cycle is linked to carbon fluxes and the partitioning of both major and minor elements in the ocean. The sensors will be useful to study the biochemical pathways in vivo, i.e., to determine phosphate flux in microorganisms, in soil and also in eukaryotes. Metabolism is regulated in response to variations in phosphate supply since many reactions are coupled to phosphorylation. Thus this sensor provides a new tool to characterize phosphate homeostasis in healthy and diseased conditions. It can be used as a tool to develop new chemicals that positively or negatively affect phosphate homeostasis in high throughput screens. It can be used to characterize cellular uptake and release, and more importantly intracellular compartmentation. At present, e.g. phosphate exchange between ER and cytosol of liver cells is not understood. The sensors can be used, to study phosphate homeostasis in the ER during hepatocytes glucose metabolism, storage and mobilization phases. The sensors can be used to characterize the unusual link between phosphate and glutamate transport in VGLUT transporters in neurons and may help elucidating important aspects of neurotransmission in healthy and diseased conditions, i.e. the link between glutamate secretion and phosphate uptake and thus may be of relevance for all diseases linked to glutamergic transmission.

It is important for an organism to maintain inorganic phosphate homeostasis. An excess or deficiency of phosphate may each cause various disorders. Renal disease can lead to loss of phosphate, resulting in diseases such as X-linked hypophosphatemia (XLH), autosomal dominant hypophosphatemic rickets (ADHR), hereditary hypophosphatemic rickets with hypercalciuria (HHRH) and oncogenic hypophosphatemic osteomalacia (OHO) (Tenenhouse and Murer, 2003, J. Am. Soc. Nephrol. 14: 240-247). This is because the kidney plays a major role in clearing and retaining inorganic phosphate in the body. Physiological studies have shown that the proximal tubule reabsorbs a bulk of the phosphate filtered through the kidney. Phosphate reabsorption in the proximal tubule is mediated by phosphate transporters. Malfunction of these phosphate transporters leads to the inhibition of phosphate reabsorption, which in turn leans to phosphate wasting.

On the other hand, elevated levels of the mineral phosphate may signal an increased risk of death for patients with chronic kidney disease. A recent study has shown that elevated phosphate levels are associated with increased mortality risk in chronic kidney disease (Kestenbaum et al. 2005, J. Am. Soc. Nephrol., 16: 520-528). Therefore, elevated levels of phosphate can be considered as an important danger sign in chronic kidney disease. Phosphate toxicity can occur when laxatives or enemas that contain phosphate are used in high doses. For all these and other cases, the sensors may provide tools to investigate the underlying defects and to develop cures.

Phosphate, as for many microorganisms, is an essential macronutrient for plant cells. The sensors may provide a means to determine the soil phosphate levels in the filed as well as the fertilization status of the plant. The sensor will help in the elucidation of mechanisms for phosphate homeostasis in plants and help in the design of improved crops with better phosphate efficiency.

Transgenic organisms expressing FLIPPi can be used to detect phosphate activity directly in organ slices or whole organisms as demonstrated for the calcium FRET indicator in *Caenorhabditis elegans* neurons (Kerr, R., Lev-Ram, V., Baird, G., Vincent, P., Tsien, R. Y., and Schafer, W. R. (2000) *Neuron* 26(3), 583-594). The phosphate sensors of the present invention are excellent tools for drug discovery and screening. Phosphate levels may be measured in real time in response to chemicals, metabolic events, transport steps and signaling processes.

The following examples are provided to describe and illustrate the present invention. As such, they should not be construed to limit the scope of the invention. Those in the art will well appreciate that many other embodiments also fall within the scope of the invention, as it is described hereinabove and in the claims.

EXAMPLES

Example 1

Cloning and Structural Modeling of PiBP

The bacterial PiBP functions as a high-affinity in vitro Pi sensor when coupled to environmentally-sensitive small fluorophore dyes (De Lorimier, R. M., Smith, J. J., Dwyer, M. A., Looger, L. L., Sali, K. M., Paavola, C. D., Rizk, S. S., Sadigov, S., Conrad, D. W., Loew, L., and Helling a, H. W. (2002) *Protein Sci* 11(11), 2655-2675). Therefore, we chose to use this polypeptide to construct a genetically-encoded nanosensor capable of reporting changes in the intracellular concentrations of Pi. Given that proteins from thermophilic organisms show enhanced stability under harsh environmental conditions and conceivably provide a more robust framework for nanosensor construction (see Application Ser. No. 60/658, 142, which is herein incorporated by reference), we chose a thermophilic strain of *Synechococcus* isolated from the hot springs of Yellowstone National Park as the source for PiBP.

To clone the PiBP gene from *Synechococcus*, a truncated PiBP (protein accession NP_415188), encoding the predicted mature protein without the signal sequence, was amplified by PCR from *Synechococcus* genomic DNA using the primers 5'-ATTGGTACCGTAGGATTTCTAACAGCG-3' (SEQ ID NO: 1) and 5'-ATAGGTACCGTTAACGG TGATG-GAATC-3' (SEQ ID NO: 2). The PCR fragment was cloned into the KpnI site of FLIPmal-25μ (Fehr, M., Frommer, W. B., and Lalonde, S. (2002) *P Natl Acad Sci USA* 99(15), 9846-9851) in pRSET-B (Invitrogen, USA), exchanging the sequence encoding the maltose-binding protein with that of PiBP. The resulting plasmid was named pRSET-FLIPPi-250n.

To improve maturation proficiency and the performance of the sensor (with respect to pH and chloride tolerance), enhanced YFP in pRSET-FLIPPi-250n was replaced with the coding sequence of the YFP variant designated Venus (forming FLIPPi-WT) (SEQ ID NO: 5 (gene) and SEQ ID NO: 6 (protein)) (Nagai, T., Ibata, K., Park, E. S., Kubota, M., Mikoshiba, K., and Miyawaki, A. (2002) *Nat Biotechnol* 20(1), 87-90). Affinity mutants (verified by sequencing the mutant DNA fragments) for FLIPPi were created by site-directed mutagenesis (Kunkel, T. A., Roberts, J. D., and Zakour, R. A. (1987) *Methods in Enzymology* 154, 367-382), generating the T22A, S52A, G162A and T163A variant sensor proteins. These pRSET-FLIPPi constructs were introduced into *E. coli* BL21(DE3) Gold (Stratagene, USA) by electroporation and the expressed proteins were extracted and purified as described (Fehr, M., Frommer, W. B., and Lalonde, S. (2002) *P Natl Acad Sci USA* 99(15), 9846-9851). For expression in the cytosol of CHO cells, DNA fragments containing FLIPPi-5μ and FLIPPi-30m sequences were excised from pRSET-FLIPPi-5μ and pRSET-FLIPPi-30m with BamHI/HindIII and cloned into pcDNA3.1 (Invitrogen, USA).

Figure 1:
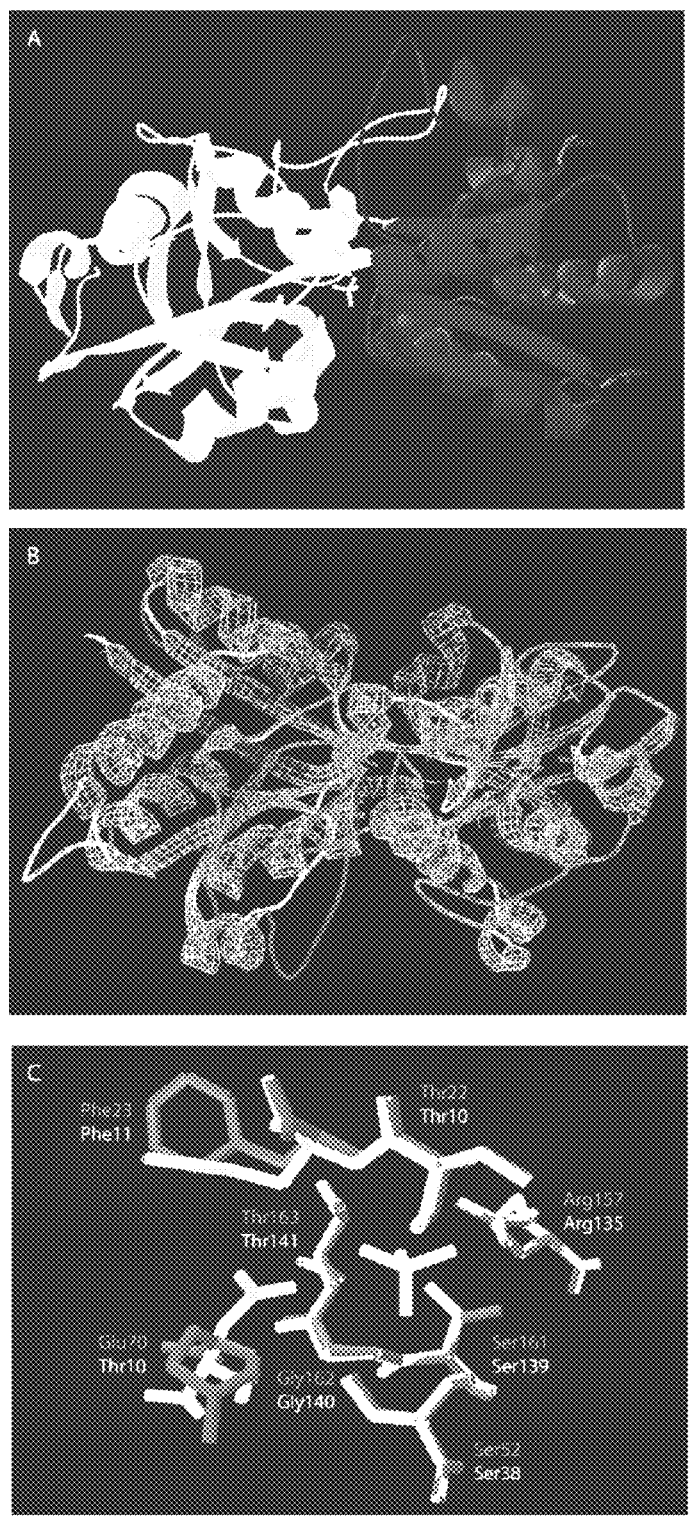
FIG. 1 shows the predicted structure of Synechococcus PiBP and the alignment with E. coli PiBP (PDB 1a40) on both protein structure and binding sites. (A) Phosphate-binding protein structure, predicted by 3D-JIGSAW server and plotted by Deepview. The substrate phosphate is light and C- and N-terminus dark. (B) Alignment of the predicted protein structure with the crystal structure of *E. coli*. (C) Alignment of binding sites. The only difference is Glu70 on FLIPPi and Thr10 on *E. coli*.

The sequence of the *Synechococcus* sp. PiBP was aligned with PiBP of *E. coli* (encoded by pstS: PDB 1a40, identity 36.9%) (De Lorimier, R. M., Smith, J. J., Dwyer, M. A., Looger, L. L., Sali, K. M., Paavola, C. D., Rizk, S. S., Sadigov, S., Conrad, D. W., Loew, L., and Helling a, H. W. (2002) *Protein Sci* 11(11), 2655-2675), and the putative periplasmic leader sequence was removed from the sequence prior to structural prediction analyses. The *Synechococcus* sp. PiBP structure was modeled using the automated prediction algorithm resident on the 3D-JIGSAW server. FIG. 1 shows the predicted polypeptide structure (A), along with the Deepview v3.7SP5 alignment of this structure with that of *E. coli* PiBP (B). The tertiary structure shown is similar to that of the *E. coli* PiBP, which provided a sound foundation for sensor construct.

Example 2

In Vitro Characterization of Nanosensors

A DNA fragment encoding the mature *Synechococcus* sp. PiBP protein was fused between the ECFP and Venus sequences as described above. The chimeric gene was expressed in *E. coli* and the protein product purified via the N-terminal His$_6$ tag using Ni$^{2+}$ affinity chromatography.

Figure 2:
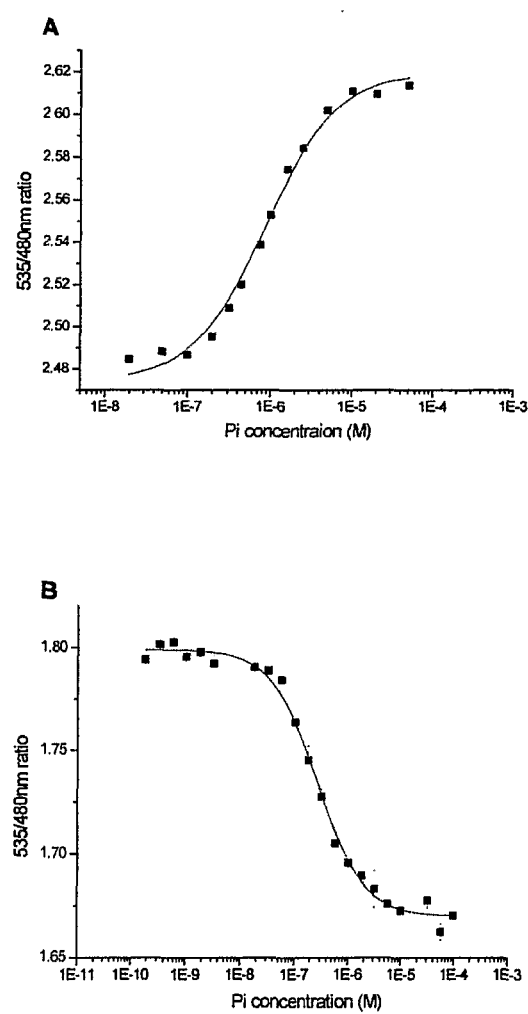
FIG. 2 shows graphs of in vitro substrate-induced FRET changes of nanosensors purified from BL21(DE3) gold. (A) FLIPPi-WT titrated with phosphate solutions. (B) Phosphate titration curve for FLIPPi-260n. The fitting curves are obtained by non-linear regression.

Addition of Pi to the purified protein resulted in a decrease in CFP and an increase in Venus emission, suggesting that binding of Pi to the chimeric sensor, designated FLIPPi-WT, resulted in a conformational change that changed the distance/orientation of the chromophores on the engineered protein. The binding constant ($K_d$) of this sensor for Pi was determined to be 840 nM and the Hill coefficient was 1.03, which is consistent with 800 nM $K_d$ as reported for the *E. coli* PiBP by Medveczky et al. (Medveczky, N., and Rosenberg, H. (1970) *Biochim Biophys Acta* 211(2), 158). As shown in FIG. 2A, the maximum ratio change observed for FLIPPi-WT is 0.14.

Figure 3:
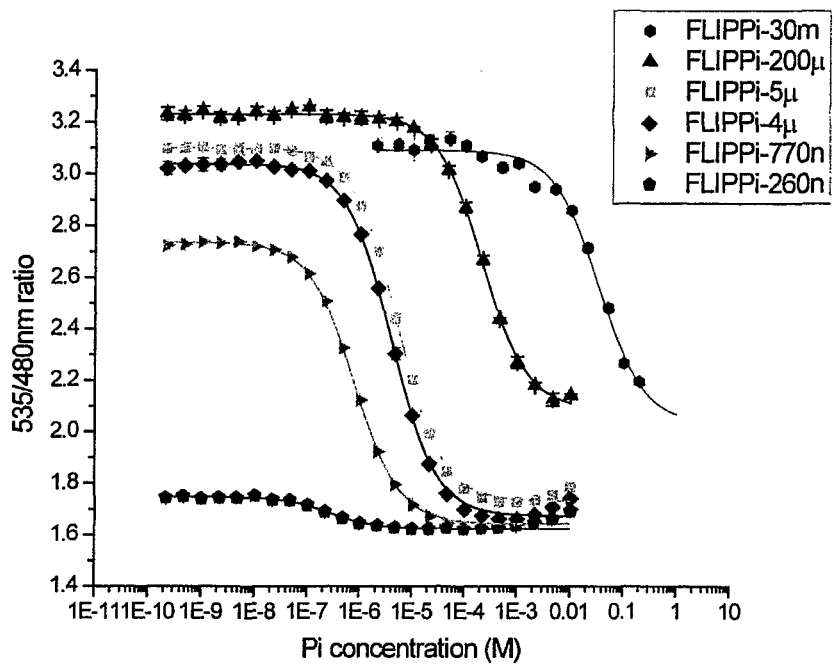
FIG. 3 is a graph showing in vitro substrate-induced FRET changes of FLIPPi affinity mutants. The fitting curves were obtained by non-linear regression.
Figure 8:
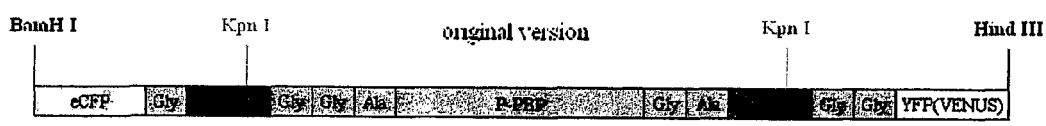
FIG. 8 is a diagram showing the deletions and the structure of the shortened FLIPPi-WT nanosensor containing deletions of material from the attached fluorophores.
Figure 8:

In attempts to modify the properties of the FLIPPi-WT nanosensor, 9 amino acids were deleted from the C-terminus of the CFP and 1 amino acid was deleted from the N-terminus of VENUS. Furthermore, four amino acids in the linker domain attaching the fluorophores to the Pi-binding domain were also removed. In total, the protein was shorted by 18 amino acids. The deletions and the structure of the shortened polypeptide are shown in FIG. 8. As shown in FIG. 3, titration of the modified protein, designated FLIPPi-260 nm, with Pi caused a CFP emission increase and Venus emission decrease, resulting in a Pi-dependant decrease in FRET. The binding constant for Pi was determined as 260 nM, with a maximum ratio change of 0.13. This change was slightly reduced relative to that of the original FLIPPi-WT fusion protein.

To expand the dynamic range of the Pi sensor, site directed mutagenesis was used as described above to lower the binding affinity of the Pi binding domain. The Pi present in the binding pocket of PiBP is held in place by strong hydrogen bonds (Luecke, H., and Quiocho, F. A. (1990) *Nature* 347(6291), 402-406). The three dimensional spatial structure of the ligand-binding pocket of FLIPPi-260n was aligned to the *E. coli* PiBP crystal structure, PDB 1a40 (Wang, Z. M., Choudhary, A., Ledvina, P. S., and Quiocho, F. A. (1994) *J Biol Chem* 269(40), 25091-25094; Ledvina, P. S., Tsai, A. L., Wang, Z. M., Koehl, E., and Quiocho, F. A. (1998) *Protein Sci* 7(12), 2550-2559). The analysis showed that the Pi binding site of FLIPPi-260n is very similar to that of *E. coli* except that the conserved Asp56 of the *E. coli* protein corresponds to Glu70 of FLIPPi-260n (FIG. 1C). Asp56 of the *E. coli* protein is considered to play a key role in recognizing both monobasic and dibasic Pi (Wang, Z. M., Choudhary, A., Ledvina, P. S., and Quiocho, F. A. (1994) *J Biol Chem* 269(40), 25091-25094).

Five residues of FLIPPi-260n were selected for site-directed mutagenesis. Mutation of amino acids predicted to reside in the Pi-binding site of FLIPPi-260n generated a set of sensors that were sensitive over a broad range of Pi concentrations, with significantly greater maximum ratio changes upon Pi binding (see Table 1). The affinity mutants were designated FLIPPi-770n, FLIPPi-4μ, FLIPPi-5μ, FLIPPi-200μ, and FLIPPi-30m, according to their $K_d$ for Pi. The Hill coefficient for all of these PiBPs was determined to be close to 1, which agrees with that reported by Medveczky et al. and indicates that there is no cooperativity in substrate binding (Medveczky, N., and Rosenberg, H. (1970) *Biochim Biophys Acta* 211(2), 158).

TABLE 1

FLIPPi affinity mutants. Binding constants determined in vitro.

| Name of sensor | Mutation form | $K_d$ (M) | $\Delta R_{max}^a$ | Hill coefficient | Range for quantification[b] | $R^2$ (n ≥ 3) |
|---|---|---|---|---|---|---|
| FLIPPi-260n | Wild type | $2.6 \times 10^{-7}$ | −0.13 | 1.03 | 25.9-1260 nM | 0.9953 |
| FLIPPi-770n | S161A | $7.7 \times 10^{-7}$ | −1.07 | 1.03 | 85.7-5650 nM | 0.9989 |
| FLIPPi-4μ | T163A | $3.9 \times 10^{-6}$ | −1.34 | 1.02 | 0.382-25.2 μM | 0.9989 |
| FLIPPi-5μ | S52A | $5.1 \times 10^{-6}$ | −1.33 | 1.03 | 0.516-34.0 μM | 0.9994 |
| FLIPPi-200μ | G162A | $2.1 \times 10^{-4}$ | −1.13 | 1.00 | 252-1660 μM | 0.9991 |
| FLIPPi-30m | T22A | 0.033 | −1.03 | 1.03 | 3.08-169 mM | 0.9882 |

[a] $\Delta R_{max}$, in vitro maximum change in ratio between absence and saturation of the binding protein
[b] Range of concentration for which a FLIPPi sensor can be used. The range for quantification was defined as the range between 10% and 90% saturation.

Each PiBP binds one molecule of Pi. Introducing substitution S161A into the PiBP moiety of FLIPPi-260n yielded FLIPPi-770n, which has a binding constant for Pi of 770 nM and can be used for quantifying Pi levels that range 0.0847 and 5.65 μM. FLIPPi-770n had a 4-fold wider measuring range and an 8-fold increase in the maximum ratio change ($\Delta R_{max}$=−1.07) relative to those of the FLIPPi-260n polypeptide (range of 25.9-1260 nM and $\Delta R_{max}$=−0.13). All the affinity mutants that were examined (Table 1) had maximum ratio change improvement of 8-10 fold. FLIPPi-4μ and FLIPPi-5μ, carrying the substitutions of T163A and S52A, respectively, had similar $K_d$ (3.9 μM for FLIPPi-4μ and 5.1 μM for FLIPPi-5μ), $\Delta R_{max}$ (−1.34 and 1.33), and quantification range (0.382 to 25.2 μM and 0.516 to 34.0 μM). FLIPPi-200μ (G162A substitution) is suitable for Pi quantification in the micromolar range (252 to 1660 μM, $K_d$=210 μM). The sensor with the best range for monitoring in vivo Pi concentrations is FLIPPi-30m. This sensor can be used over the range of 3.08 to 169 mM, Pi, which generally spans the intracellular concentration.

Example 3

Substrate Binding Specificity

Measuring substrate concentration in complex mixtures (e.g. cytoplasm of a living cell) requires sensors with high specificity towards their substrate. Therefore, for in vivo applications, it is necessary to test the binding specificity of each of the sensors.

Figure 4:
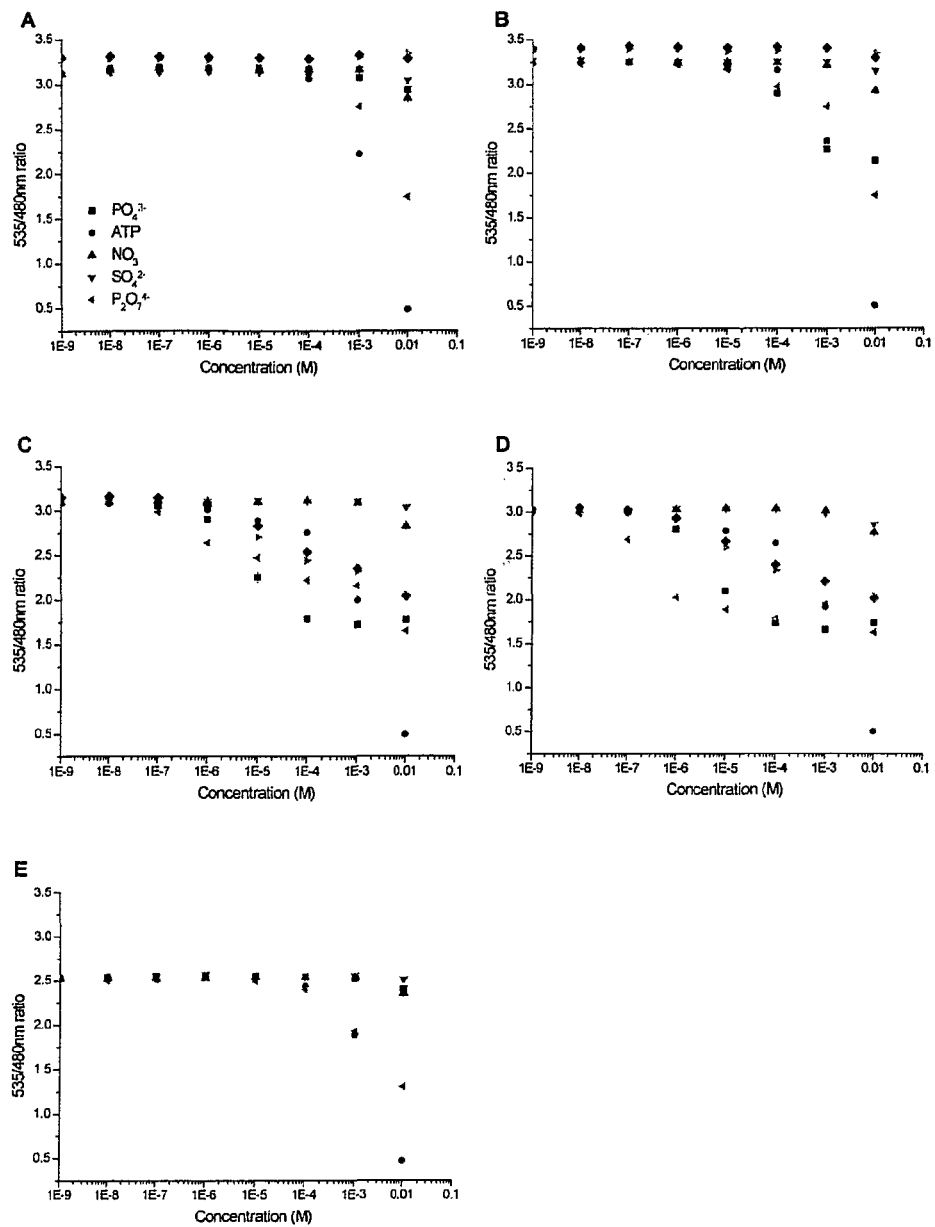
FIG. 4 contains graphs showing the results of binding specificity assays for the affinity mutants. All the sensors were titrated with solutions of sulfate, nitrate, phosphate, pyrophosphate and ATP. (A) FLIPPi-30m. (B) FLIPPi-200-µ. (C) FLIPPi-5µ. (D) FLIPPi-4µ. (E) FLIPglu-600µ as control.

FRET characteristics of FLIPPi-4μ, FLIPPi-5μ, FLIPPi-200μ, and FLIPPi-30m were monitored at different concentrations of Pi and with potential nonspecific substrates, including sodium sulfate, sodium nitrate, ATP, sodium pyrophosphate. The FRET assays were performed in microtitre plates (FIG. 4A-D), with the glucose sensor FLIPglu-600μ (Fehr, M., Lalonde, S., Lager, I., Wolff, M. W., and Frommer, W. B. (2003) *J Biol Chem* 278(21), 19127-19133) used as a control (FIG. 4E).

Figure 5:
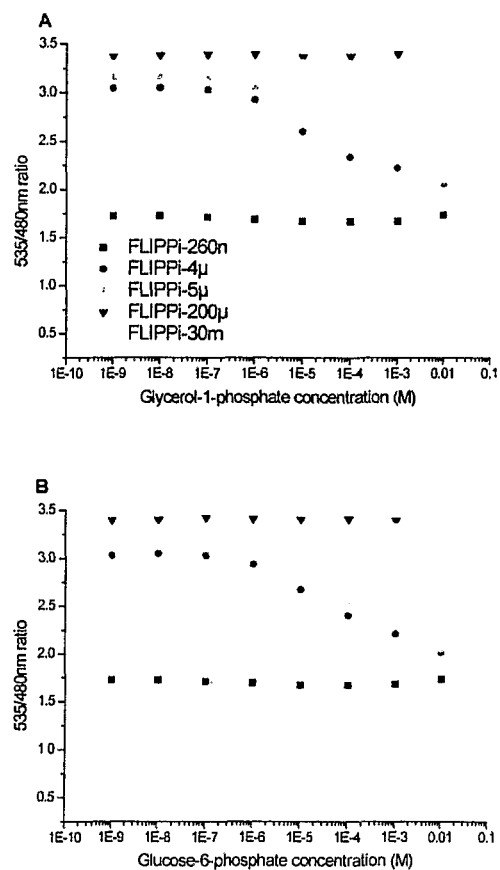
FIG. 5 contains graphs showing the results of further binding specificity assays for the affinity mutants. FLIPPi sensors were titrated with glycerol-1-phosphate and glucose-6-phosphate solutions. (A) Titration with glycerol-1-phosphate. (B) Titration with glucose-6-phosphate.

FLIPPi-30m, FLIPPi-200μ and the control FLIPglu-600μ did not bind the four nonspecific substrates. FLIPPi-4μ and FLIPPi-5μ responded to pyrophosphate, with lower binding constants than those for Pi, while these sensors did not respond to the other three substrates. ATP seemed to be a quencher to all FLIPPi sensors tested, and pyrophosphate was another quencher to FLIPPi-30m and FLIPPi-200μ. Glycerol-1-phosphate and glucose-6-phosphate were also used for specificity tests with FLIPPi-4μ, FLIPPi-5μ, FLIPPi-200μ, and FLIPPi-30m together with the wild type FLIPPi-260n (FIG. 5). The results demonstrate that while FLIPPi-200-μ, FLIPPi-30m with FLIPPi-260n did not respond to either substrate, these substrates did affect the fluorescence emission ratios for FLIPPi-4μ and FLIPPi-5μ.

Example 4

In Vivo Characterization of Nanosensors

To demonstrate in vivo application of FLIPPi sensors, pRSET-FLIPPi-30m and pRSET-FLIPPi-5μ sequences were cloned in pcDNA3.1 and transfected into CHO cells. The CHO cells were grown overnight after transfection and then starved for Pi for 16 h by replacing the Pi-replete growth medium with modified Tyrode's saline solution containing no Pi. Cells expressing FLIPPi-30m were perfused with increasing concentrations of external Pi along a specific step schedule (FIG. 6) and changes in the fluorescence ratio were monitored. Furthermore, after a constant fluorescence ratio was attained at each Pi concentration, the Pi was removed by perfusion with Pi-free solution. Cells transfected with FLIPPi-5μ was used as control because of its high affinity for Pi.

Figure 6:
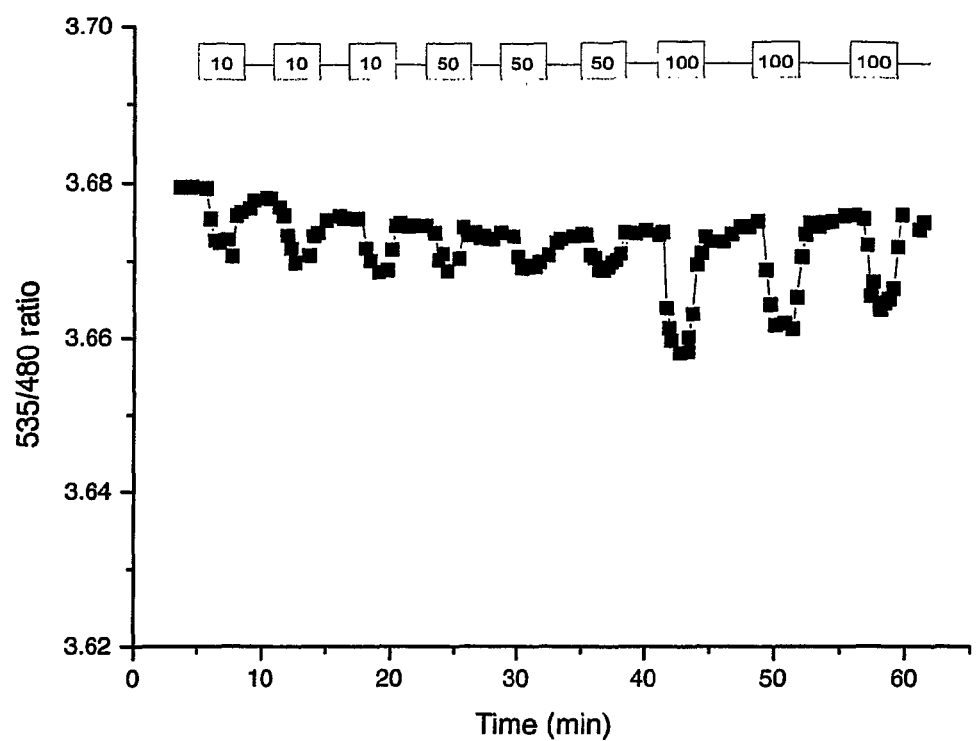
FIG. 6 shows the FRET ratio change of FLIPPi-30m nanosensor in CHO cells in response to 10 µM, 50 µM and 100 µM phosphate perfusions. Each phosphate perfusion was 2 min, followed by 3 min wash with the phosphate-free modified Tyrode's saline solution. The numbers in the box indicates the concentration of phosphate solution used.

Cells grown under normal growth conditions, no matter which FLIPPi sensor was expressed, did not show a signal change upon perfusion with up to 10 mM Pi (data not shown). Starved cells expressing FLIPPi-30m responded to solutions containing 10 μM, 50 μM and 100 μM Pi; the highest ratio change was for 100 μM Pi ratio changes (FIG. 6). Starved control cells did not show any VENUS/CFP ratio change when perfused with same Pi solutions.

All publications, patents and patent applications discussed herein are incorporated herein by reference. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

---

What is claimed:

1. An isolated nucleic acid which encodes a phosphate fluorescent indicator comprising:
    a phosphate binding protein moiety polypeptide from a type II phosphate periplasmic binding protein comprising a first and a second globular domain separated by a hinge, the phosphate binding moiety having at least 95% identity to the amino acid sequence as set forth in SEQ ID NO: 4 and wherein the first globular domain comprises the amino and carboxyl termini of the phosphate binding protein moiety;
    a donor fluorescent protein moiety fused to the amino terminus of the phosphate binding protein moiety; and
    an acceptor fluorescent protein moiety fused to the carboxyl terminus of the phosphate binding protein moiety;
    wherein fluorescence resonance energy transfer (FRET) between the donor moiety and the acceptor moiety is altered when the donor moiety is excited and phosphate binds to the phosphate binding protein moiety.

2. The isolated nucleic acid of claim 1, wherein said phosphate binding protein moiety comprises the amino acid sequence of SEQ ID NO: 4.

3. The isolated nucleic acid of claim 1, wherein said donor fluorescent protein moiety is selected from the group consisting of a green fluorescent protein (GFP), a cyan fluorescent protein (CFP), a blue fluorescent protein (BFP), a yellow fluorescent protein (YFP), a dsRED, CoralHue Midoriishi-Cyan (MiCy) and monomeric CoralHue Kusabira-Orange (mKO).

4. The isolated nucleic acid of claim 1, wherein said acceptor fluorescent protein moiety is selected from the group consisting of a GFP, a $CFP_5$ a BFP, a YFP, a dsRED, CoralHue Midoriishi-Cyan (MiCy) and monomeric CoralHue Kusabira-Orange (mKO).

5. The isolated nucleic acid of claim 1, wherein said donor fluorescent protein moiety is a CFP and said acceptor fluorescent protein moiety is YFP Venus.

6. The isolated nucleic acid of claim 1, further comprising at least one linker moiety.

7. The isolated nucleic acid of claim 6, further comprising a deletion, insertion or mutation of one or more amino acids in said phosphate binding protein moiety, said donor fluorescent moiety, said acceptor fluorescent moiety and/or said at least one linker.

8. The isolated nucleic acid of claim 7, wherein said phosphate fluorescent indicator shows increased or decreased affinity for phosphate.

9. The isolated nucleic acid of claim 7, wherein said phosphate fluorescent indicator shows an increase in maximum FRET ratio change.

10. A cell expressing the nucleic acid of claim 1.

11. The cell of claim 10, wherein the phosphate fluorescent sensor is expressed in the cytosol of said cell.

12. The cell of claim 10, wherein the phosphate fluorescent sensor is expressed on the surface of said cell.

13. The cell of claim 10, wherein the phosphate fluorescent sensor is expressed in the nucleus of said cell.

14. The cell of claim 10, wherein the cell is a prokaryote.

15. The cell of claim 10, wherein the cell is a eukaryotic cell.

16. The cell of claim 15, wherein the cell is a yeast cell.

17. The cell of claim 15, wherein the cell is an animal cell.

18. An expression vector comprising the nucleic acid of claim 1.

19. A cell comprising the vector of claim 18.

20. The expression vector of claim 18 adapted for function in a prokaryotic cell.

21. The expression vector of claim 18 adapted for function in a eukaryotic cell.

22. A phosphate binding fluorescent indicator encoded by the nucleic acid of claim 1.

23. A method of detecting changes in the level of phosphate in a sample of cells, comprising:
    (a) providing a cell expressing the nucleic acid of claim 1; and
    (b) detecting a change in FRET between said donor fluorescent protein moiety and said acceptor fluorescent protein moiety, wherein a change in FRET between said donor moiety and said acceptor moiety indicates a change in the level of phosphate in a sample of cells.

24. The method of claim 23, wherein the step of determining FRET comprises measuring light emitted from the acceptor fluorescent protein moiety.

25. The method of claim 23, wherein determining FRET comprises measuring light emitted from the donor fluorescent protein moiety, measuring light emitted from the acceptor fluorescent protein moiety, and calculating a ratio of the light emitted from the donor fluorescent protein moiety and the light emitted from the acceptor fluorescent protein moiety.

26. The method of claim 23, wherein the step of determining FRET comprises measuring the excited state lifetime of the donor moiety.

27. The method of claim 23, wherein said sample of cells is contained in vivo.

28. The method of claim 23, wherein said sample of cells is contained in vitro.

29. A method of identifying a compound that modulates the binding of a phosphate to its receptor, comprising:
    (a) contacting a cell expressing the nucleic acid of claim 1 with one or more test compounds in the presence of phosphate; and
    (b) determining FRET between said donor fluorescent domain and said acceptor fluorescent domain following said contacting, wherein increased or decreased FRET following said contacting indicates that said test compound is a compound that modulates phosphate binding.

30. The isolated nucleic acid of claim 1, wherein the phosphate binding protein comprises a mutation selected from the group consisting of S175A, T177A, S66A, G176A or T36A.

31. The isolated nucleic acid of claim 1, wherein the phosphate fluorescent indicator has at least 90% identity with the amino acid sequence as set forth in SEQ ID NO: 6.

32. The isolated nucleic acid of claim 1, wherein the phosphate fluorescent indicator has at least 95% identity with the amino acid sequence as set forth in SEQ ID NO: 6.

33. The isolated nucleic acid of claim 1, wherein the phosphate fluorescent indicator comprises the amino acid sequence as set forth in SEQ ID NO: 6.

* * * * *